United States Patent [19]

Reusser

[11] 3,971,810

[45] July 27, 1976

[54] SOLID PESTICIDAL CHLORINATED PHENOLIC CONCENTRATES

[75] Inventor: Robert E. Reusser, Bartlesville, Okla.

[73] Assignee: Phillips Petroleum Company, Bartlesville, Okla.

[22] Filed: Feb. 18, 1975

[21] Appl. No.: 550,502

Related U.S. Application Data

[63] Continuation of Ser. No. 423,457, Dec. 10, 1973, abandoned.

[52] U.S. Cl. .............................. 424/347; 424/278; 424/317; 424/354; 424/358
[51] Int. Cl.² ............................................ A01N 9/26
[58] Field of Search ............ 424/278, 317, 347, 354

[56] References Cited

UNITED STATES PATENTS

| | | | |
|---|---|---|---|
| 2,789,078 | 4/1957 | Trusler .............................. | 424/14 X |
| 3,061,508 | 10/1962 | Morriss et al. ................... | 424/347 X |
| 3,474,172 | 10/1969 | Hill et al. ............................ | 424/294 |

*Primary Examiner*—Leonard Schenkman

[57] ABSTRACT

A chlorinated phenolic concentrate in the form of a solid solution is formed by melting a carrier, which is a solid at normal ambient temperatures, dissolving a solid chlorinated phenolic derivative therein and cooling the resultant mixture.

5 Claims, No Drawings

SOLID PESTICIDAL CHLORINATED PHENOLIC CONCENTRATES

This application is a continuation of application Ser. No. 423,457, filed Dec. 10, 1973, now abandoned.

BACKGROUND OF THE INVENTION

The invention relates to a chlorinated phenolic concentrate and a method for producing the concentrate.

A number of chlorinated phenolic derivatives are used as fungicides, insecticides, herbicides and the like and more particularly these derivatives are used as wood preservatives. In using chlorinated phenolic derivatives as wood preservatives and also in various other applications, a weak solution of the derivative in a hydrocarbon diluent is used. It is desirable to use a relatively inexpensive hydrocarbon diluent in making the weak solution, such as diesel fuel, stove oil, kerosene and the like; however, the solubility of the chlorinated phenolic derivatives in such diluents is very low and forming such solutions, even in very weak concentrations, is often difficult. A common method used to form these solutions is to dissolve the derivative first in a "carrier liquid" in which the derivative has a high solubility, such as alcohol, glycol, etc., then let down this rather high concentrated solution in kerosene or other relatively inexpensive diluents. The most common disadvantage of this method is that the carrier liquids in which the derivatives have a high solubility are fairly expensive.

Other problems associated with the use of chlorinated phenolic derivatives relates to their toxicity and danger to human life. Generally these materials are solids, but they give off dust which, in varying degree are toxic, and can cause skin irritation or more serious injury. Thus, spillage during shipment or exposure while dissolving the derivatives in various liquids presents a constant danger to workmen. Also, if the derivatives are shipped as a liquid after being dissolved in a liquid carrier, then the attendant disadvantages associated with shipping hazardous liquids must be considered.

It is an object of the invention to minimize the problems in handling chlorinated phenolic derivatives.

It is also an object of the invention to minimize the problems of dissolving the derivatives in liquid diluents.

A further object of the invention is to minimize the hazardous dust associated with solid derivatives.

Other objects, aspects and advantages of the invention will be apparent to those skilled in the art upon studying the specification and appended claims.

SUMMARY OF THE INVENTION

According to the invention there is provided a chlorinated phenolic concentrate in the form of a solid homogeneous mixture comprising a carrier and a chlorinated phenolic derivative, both of which are solids at normal ambient temperatures.

Further according to the invention, there is provided a method for the preparation of a solid chlorinated phenolic concentrate which comprises melting a carrier which is a solid at normal ambient temperatures, dissolving a chlorinated phenolic derivative in the melted carrier and cooling the resultant mixture, thus forming the solid homogeneous concentrate.

DETAILED DESCRIPTION OF THE INVENTION

It has been discovered that many of the problems associated with handling solid chlorinated phenolic derivatives can be eliminated or at least minimized by the practice of the present invention. The solid concentrate described herein emits little if any dust and it is readily let down with most hydrocarbon diluents which are normally used with chlorinated phenolic derivatives. In addition, the solid concentrate is easy to produce and ship.

The chlorinated phenolic derivatives suitable for use in the practice of the invention are compounds which are solids at normal ambient temperatures. Some examples of such compounds are pentachlorophenol, dieldrin, dichlorodiphenoltrichloroethane, 2,4-(dichlorophenoxy)-acetic acid and (2,4,5-trichlorophenoxy)acetic acid.

The solid carriers suitable for use in the practice of the invention are compounds which are solids at normal ambient temperatures and which, after being melted, will dissolve the chlorinated phenolic derivatives. Suitable solid carriers are aromatic hydrocarbons such as biphenyl, 4,4'-dimethyl biphenyl, naphthalene, anthracene, 1-methyl anthracene, 2-methyl anthracene, 9-methyl anthracene, 9-ethyl anthracene, 1,3-dimethyl anthracene, phenanthrene, 9-ethyl phenanthrene, and 4,5-dimethyl phenanthrene.

Any suitable apparatus for melting the carriers and adding the derivatives can be used; however, it is recommended that a mixer be used to speed up and generally facilitate the dissolution process. Also, no additional apparatus is required to cool the resulting mixture and good results are obtained simply by allowing the heated mixture to cool at room temperature.

In the practice of the invention, the amount of chlorinated phenolic derivative in the mixture can be varied widely but generally is in the range of from about 1 to 75 weight percent, preferably from about 10 to 65 weight percent and more preferably from about 30 to 60 weight percent with the balance of the mixture being the carrier. It is, of course, desirable to minimize the amount of carrier in the concentrate and at the same time retain the properties imparted to the concentrate due to the presence of carrier.

As previously noted, the concentrates of the present invention are let down in relatively inexpensive liquids or, as referred to herein, diluents. Diluents frequently used are paraffinic hydrocarbon liquids of from 5 to 12 carbon atoms per molecule such as pentane, octane, decane, and dodecane; cycloparaffins such as cyclohexane; aromatics such as benzene and toluene. Mixtures of suitable diluents can also be used. However, the most commonly used diluents are liquids such as stove oil, diesel fuel, kerosene, or mixtures thereof.

As used herein, the term "normal ambient temperature" means a temperature of from about 0 to 50°C. The term "carrier" is used herein to mean any hydrocarbon compound which is a solid at normal ambient temperatures and which, when melted, dissolves the chlorinated phenolic derivative to form the solid concentrate upon cooling of the resultant mixture.

It is noted that the presence of the carrier while letting down the concentrate in a diluent, such as kerosene and stove oil, promotes the dissolution of the chlorinated phenolic derivative to an unexpected degree as will be shown more specifically by the following examples.

EXAMPLES

The first four examples serve to illustrate the preparation of a concentrate using various carriers with the chlorinated phenolic derivative pentachlorophenol. The remaining examples demonstrate by comparative results the relative ease in which the solid concentrate is let down with suitable diluents compared with dissolving pentachlorophenol alone with the same diluents. Also, it should be mentioned that in calculating the weight percent of derivative in the diluent, the amount of carrier present in the mixture is ignored.

EXAMPLE I 51.4 Grams of biphenyl was heated to about 80°C and 77.1 grams of pentachlorophenol was slowly added. The mixture was further heated to 110°C (which is well below the melting point of 190°C of pentachlorophenol) and also stirred for about 30 minutes. The resultant dark brown liquid was allowed to cool and at 65°C it solidified into a 60 weight percent pentachlorophenol-40 weight percent biphenyl homogeneous concentrate. The concentrate emitted little or no dust.

EXAMPLE II 4.15 Grams of naphthalene was melted in a test tube and 6.00 grams of pentachlorophenol was added. The mixture was stirred for 2 to 3 minutes at a temperature of about 105°C, producing a dark brown homogeneous melt. The solution was poured into an aluminum dish and allowed to cool. A brittle, grayish-tan solid formed at 75°C. The solid contained 59.1 weight percent derivative and showed no signs of dustiness.

EXAMPLE III 3.70 Grams of phenanthrene and 5 grams of pentachlorophenol were combined as in Example II. Homogenization was complete at about 115°C and the dark brown solution began to solidify at about 80°C. The mixture had a pentachlorophenol content of 57.4 weight percent and was not dusty.

EXAMPLE IV 5.9 Grams of anthracene and 8.3 grams of pentachlorophenol were combined as in Example II. At about 185°C, homogenization was complete and the mixture formed a gray, brittle solid upon cooling. The derivative content of the mixture was 58.4 weight percent and it was not dusty.

EXAMPLE V

The solubility of the concentrate produced in Example I was tested in stove oil. Table I shows the properties of the particular stove oil used.

TABLE I

| Stove Oil Distillation | |
|---|---|
| Amount Vaporized, % | Boiling Point, °F |
| Initial Boiling Point | 359 |
| 5 | 390 |
| 10 | 397 |
| 15 | 397 |
| 20 | 405 |
| 30 | 413 |
| 40 | 422 |
| 50 | 429 |
| 60 | 440 |
| 70 | 448 |
| 80 | 459 |
| 90 | 476 |
| 95 | 490 |
| End Boiling Point (determined by ASTM D-86-61) | 508 |
| Other Properties | |
| API Gravity 60°F | = 44.0 |
| Specific Gravity 60°/60°F | = 0.8063 |
| Density lb/gal. 60°F | = 6.713 |
| Freezing Point | = −46 to −50°F |
| Kauri-Butanol Solubility (determined according to ASTM D-1133-61) | = 32.7 |
| Aniline Point (determined according to ASTM D-1012) | = 149.2 |

5.6 Grams of the 60 percent pentachlorophenol in biphenyl concentrate was added to 67.2 grams of the stove oil at ambient temperature to produce approximately a 5 weight percent solution. The stove oil was stirred during the addition of concentrate. The mixture was allowed to stand overnight. Examination subsequently revealed that all of the biphenyl and all but an estimated 3 to 4 percent of the pentachlorophenol had completely dissolved.

EXAMPLE VI

As a comparison with Example V, 3.62 grams of pentachlorophenol was added to 72.5 grams of stove oil as above in order to make approximately a 5 percent by weight solution. After allowing the mixture to stand overnight at room temperature, only an estimated 50 percent of the derivative had dissolved.

In comparing Examples V and VI it is seen the relative ease in which a 5 percent solution of pentachlorophenol in stove oil can be made using the present invention. In addition it is noted that the solution per the present invention was made without the danger of pentachlorophenol dust.

EXAMPLE VII

Approximately 3 weight percent solution was made using 1.45 grams of the concentrate of Example I and 29.1 grams of stove oil at ambient temperature. After the mixture was shaken for 15 minutes, all of the concentrate had dissolved, producing a composition suitable for use as a wood-treating preservative.

EXAMPLE VIII

As a comparison with Example VII, an attempt was made to make a 3 weight percent solution using 37.9 grams of stove oil at ambient temperature and 1.14 grams of pentachlorophenol. After shaking the mixture for 15 minutes, less than 50 percent of the derivative had dissolved. The mixture was placed on a shaking machine for 5 hours and an estimated 15 to 25 percent of the pentachlorophenol remained undissolved. The mixture was re-examined after standing for 24 hours at room temperature and the same quantity of derivative appeared to be undissolved.

A comparison of Examples VII and VIII indicates the utility of the present invention even where very weak solutions of pentachlorophenol are desired.

EXAMPLE IX

Experiments similar to the above were repeated but using kerosene rather than stove oil as the diluent. The properties of the kerosene used are shown in Table II below.

TABLE II

| Kerosene Distillation | |
|---|---|
| Amount Vaporized, % | Boiling Point, °F |
| Initial Boiling Point | 320 |
| 5 | 345 |
| 10 | 355 |
| 15 | 358 |
| 20 | 367 |
| 30 | 381 |
| 40 | 395 |
| 50 | 409 |
| 60 | 424 |
| 70 | 442 |
| 80 | 461 |
| 90 | 488 |
| 95 | 512 |
| End Boiling Point | 550 |
| (determined by ASTM D-86-61) | |

| Other Properties | |
|---|---|
| API Gravity 60°F | = 44.8 |
| Specific Gravity 60°/60°F | = 0.8026 |
| Density lb/gal. 60°F | = 6.682 |
| Freezing Point | = −56 to −60°F |
| Kauri-Butanol Solubility (determined according to ASTM D-1133-61) | = 34.6 |
| Aniline Point (determined according to ASTM D-1012) | = 143.8 |

An attempt was made to prepare a 5 weight percent solution of pentachlorophenol in kerosene at ambient temperature using 2.63 grams of the derivative in 50.5 grams of kerosene. After shaking the mixture on a shaking machine for 6 hours and allowing the mixture to stand for several days, a portion of the derivative was still undissolved.

EXAMPLE X

In comparison with Example IX, 7.68 grams of the concentrate of Example I was combined with 58.4 grams of kerosene at ambient temperature to make a solution approximately 7 weight percent. After shaking the mixture as above for 6 hours and allowing it to stand for several days, some solids were present, but it was visually determined that this solution contained less solids than did the solution in Example IX even though a 7 percent concentration was attempted instead of the 5 percent solution of Example IX.

EXAMPLE XI

A 10 percent by weight mixture was made by adding 6.05 grams of pentachlorophenol to 54.4 grams of kerosene at ambient temperature. After 6 hours on a shaking machine, a considerable amount of the derivative remained undissolved.

EXAMPLE XII

In comparison with Example XI, 14.32 grams of the concentrate of Example I was added to 51.6 grams of kerosene at ambient temperature. After shaking the mixture approximately 6 hours a considerable amount of solid remained undissolved.

From the results of Examples XI and XII, it was concluded that the solubility of pentachlorophenol in kerosene had been exceeded. However, Examples IX and X clearly show the advantage of using the concentrate in kerosene.

The above examples demonstrate the ease in which the concentrate is made and the relatively dust-free character of the concentrate. Also, they show that pentachlorophenol can be solubilized in diluents more readily and completely where the concentrate of the invention is used.

What is claimed is:

1. A pesticidal chlorinated phenolic concentrate in the form of a solid homogeneous mixture prepared by:
   heating an aromatic hydrocarbon carrier to its melting point, said carrier being a solid at temperatures in the range of from about 0° to 50°C;
   dissolving a chlorinated phenolic derivative in the melted carrier, said chlorinated phenolic derivative being a solid at temperatures in the range of from about 0° to 50°C; and
   cooling the resultant mixture to form said concentrate;
   said concentrate comprising from about 1 to 75 weight percent of said chlorinated phenolic derivative and 99 to 25 weight percent of said carrier.

2. The concentrate of claim 1 wherein the aromatic hydrocarbon carrier is selected from the group consisting of biphenyl, 4,4'-dimethyl biphenyl, naphthalene, anthracene, 1-methyl anthracene, 2-methyl anthracene, 9-methyl anthracene, 9-ethyl anthracene, 1,3-dimethyl anthracene, phenanthrene, 9-ethyl phenanthrene, and 4,5-dimethyl phenanthrene, and wherein the chlorinated phenolic derivative is selected from the group consisting of pentachlorophenol, dieldrin, dichlorodiphenoltrichloroethane, 2,4-(dichlorophenoxy)acetic acid and (2,4,5-trichlorophenoxy)acetic acid.

3. The concentrate of claim 1 comprising from about 10 to 65 weight percent chlorinated phenolic derivative and 90 to 35 weight percent carrier.

4. The concentrate of claim 3 comprising from about 30 to 60 weight percent chlorinated phenolic derivative and 70 to 40 weight percent carrier.

5. The concentrate of claim 4 wherein the chlorinated phenolic derivative is pentachlorophenol and the carrier is biphenyl.

* * * * *